United States Patent [19]

Kropp et al.

[11] 4,324,725
[45] * Apr. 13, 1982

[54] PREPARATION OF 5-(2,2-DIHALOVINYL)-4,4-DIALKYL-TETRAHYDRO-FURAN-2-ONES

[75] Inventors: Rudolf Kropp, Limburgerhof; Martin Fischer, Ludwigshafen; Klaus Halbritter, Mannheim, all of Fed. Rep. of Germany

[73] Assignee: BASF Aktiengesellschaft, Fed. Rep. of Germany

[*] Notice: The portion of the term of this patent subsequent to Mar. 16, 1999, has been disclaimed.

[21] Appl. No.: 178,177

[22] Filed: Aug. 14, 1980

[30] Foreign Application Priority Data

Sep. 19, 1979 [DE] Fed. Rep. of Germany ....... 2937763

[51] Int. Cl.³ .......................................... C07D 307/32
[52] U.S. Cl. ............................ 260/343.6; 260/347.7; 260/326.5 D; 546/214; 544/152; 204/158 R; 204/158 HA
[58] Field of Search .......... 260/343.6, 347.7, 326.5 D; 546/214; 544/152; 204/158, 158 HA

[56] References Cited

U.S. PATENT DOCUMENTS

| | | | |
|---|---|---|---|
| 3,884,916 | 5/1975 | Janssen et al. .................. | 260/347.7 |
| 4,102,896 | 7/1978 | Raphael ............................ | 260/343.6 |
| 4,195,033 | 3/1980 | Punja ................................ | 260/343.6 |
| 4,215,050 | 7/1980 | Lantzsch ......................... | 260/343.6 |

FOREIGN PATENT DOCUMENTS

| | | | |
|---|---|---|---|
| 2621831 | 12/1976 | Fed. Rep. of Germany ... | 260/343.6 |
| 2623777 | 12/1976 | Fed. Rep. of Germany ... | 260/343.6 |
| 2624351 | 12/1977 | Fed. Rep. of Germany ... | 260/343.6 |
| 52-57163 | 5/1977 | Japan ............................... | 260/343.6 |
| 52-83457 | 7/1977 | Japan ............................... | 260/343.6 |
| 52-83459 | 7/1977 | Japan ............................... | 260/343.6 |
| 1549368 | 8/1979 | United Kingdom ............. | 260/343.6 |

*Primary Examiner*—Henry R. Jiles
*Assistant Examiner*—Jane T. Fan
*Attorney, Agent, or Firm*—Keil & Witherspoon

[57] ABSTRACT

Preparation of 5-(2,2-dihalovinyl)-4,4-dialkyl-tetrahydro-furan-2-ones of the formula I

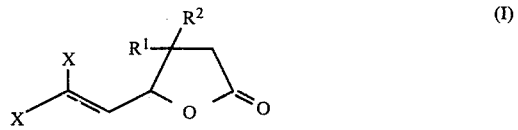

where $R^1$ and $R^2$ are each alkyl of 1 to 4 carbon atoms and X is halogen, by reacting a carboxylic acid amide of the formula II

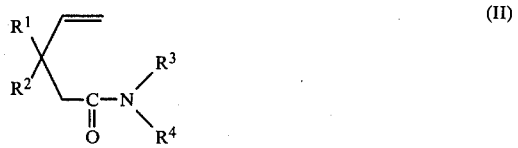

where $R^3$ and $R^4$ are each alkyl of 1 to 4 carbon atoms, aralkyl of 7 to 9 carbon atoms or aryl of 6 to 10 carbon atoms, or together with the nitrogen form a 5-membered or 6-membered saturated ring which may contain a second hetero-atom, with a carbon tetrahalide of the formula III

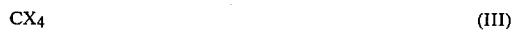

to give an iminium salt of the formula IV

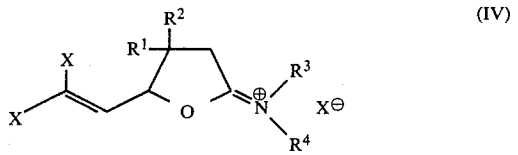

and then hydrolyzing the iminium salt; and novel iminium salts of the formula IV.

3 Claims, No Drawings

PREPARATION OF 5-(2,2-DIHALOVINYL)-4,4-DIALKYL-TETRAHYDRO-FURAN-2-ONES

The present invention relates to a process for the preparation of 5-(2,2-dihalovinyl)-4,4-dialkyl-tetrahydrofuran-2-ones by reacting N,N-disubstituted carboxylic acid amides with carbon tetrahalides and then hydrolyzing the iminium salts obtained.

Several processes for the preparation of 5-(2,2-dihalovinyl)-4,4-dialkyl-tetrahydrofuran-2-ones have been disclosed. For example, German Laid-Open Application DOS No. 2,621,831 describes the reaction of a 4,6,6,6-tetrahalo-3,3-dimethyl-hexanoic acid with an alkali metal alcoholate to give a 5-(2,2-dihalovinyl)-4,4-dimethyl-tetrahydrofuran-2-one. These lactones can also be obtained by treating an ethyl 4,6,6,6-tetrahalo-3,3-dimethyl-hexanecarboxylate with sodium hydroxide (German Laid-Open Application DOS 2,624,351), by boiling a methyl 4,6,6-trihalo-3,3-dimethyl-hex-5-enoate with water, or heating the same compound at 180°–200° C. (Japanese Laid-Open Applications 77/83,457 and 77/83,459) or by treating a 4,3,2,2-tetrahalo-5,5-dimethyl-cyclohexanone with an alkali metal hydroxide (German Laid-Open Application DOS No. 2,623,777). Another method of synthesis is an addition reaction of acetic acid with 1,1-dichloro-4-methyl-1,3-pentadiene in the presence of manganese (III) acetate (Japanese Laid-Open Application 77/57,163), to give the corresponding dichlorovinyl-substituted lactone. Disadvantages of the above processes are that the yield is in some cases low, the procedure is involved and the starting materials used are difficult to obtain.

We have found that 5-(2,2-dihalovinyl)-4,4-dialkyl-tetrahydrofuran-2-ones of the formula

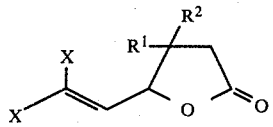

(I)

where $R^1$ and $R^2$ are each alkyl of 1 to 4 carbon atoms and X is halogen are obtained in an advantageous manner when a carboxylic acid amide of the formula II

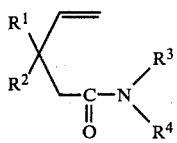

(II)

where $R^1$ and $R^2$ are each alkyl of 1 to 4 carbon atoms and $R^3$ and $R^4$ are each alkyl of 1 to 4 carbon atoms, aralkyl of 7 to 9 carbon atoms or aryl of 6 to 10 carbon atoms or together with the nitrogen on which they are present as substituents form a 5-membered or 6-membered saturated ring which may contain a further hetero-atom, is reacted with a carbon tetrahalide of the formula III

CX₄ (III)

where X is halogen, in the presence of an initiator and of an organic diluent or solvent, at from 120° to 160° C., to give an iminium salt of the formula IV

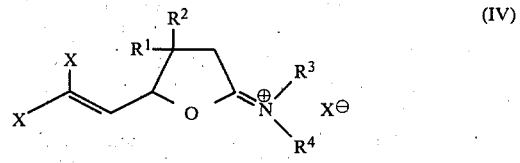

where $R^1$, $R^2$, $R^3$, $R^4$ and X have the above meanings, and this iminium salt is subsequently hydrolyzed.

The novel process may be used to prepare 5-(2,2-dihalovinyl)-4,4-dialkyl-tetrahydrofuran-2-ones which serve as intermediates for the synthesis of active ingredients for insecticides. The compounds may be converted, by treatment with an inorganic acid halide, eg. a thionyl halide, and subsequent reaction with a base, to 2-(2,2-dihalovinyl)-3,3-dialkyl-cyclopropanecarboxylic acid esters, eg. to alkyl 2-(2,2-dihalovinyl)-3,3-dimethyl-cyclopropanecarboxylates (German Laid-Open Application DOS No. 2,621,831), which are starting materials for the synthesis of pyrethroid-type active ingredients for insecticides. The synethesis of 5-(2,2-dihalovinyl)-4,4-dialkyl-tetrahydrofuran-2-ones by the novel process is particularly advantageous and economical, since it conforms to three basic prerequisites for industrial exploitation, namely easily obtainable starting materials, simplicity of operation and high yield.

The carboxylic acid amides of the formula II, used as starting materials, are known and may be prepared by methods based on conventional processes (Japanese Laid-Open Application No. 77/83,411 and German Laid-Open Application DOS No. 2,732,213). The carboxylic acid amides may also be obtained by reacting acetamide-acetals or ketene-acetal-aminals with 3-methyl-but-2-en-1-ol.

Preferred starting materials of the formula II are 3,3-dimethyl-pent-4-enoic acid N,N-dimethylamide, 3,3-diethyl-pent-4-enoic acid N,N-dimethylamide, 3-methyl-3-n-propyl-pent-4-enoic acid N,N-dimethylamide, 3,3-dimethyl-pent-4-enoic acid N-methyl-N-phenylamide, 3,3-dimethyl-pent-4-enoic acid N-methyp-N-benzylamide, 3,3-dimethyl-pent-4-enoic acid pyrrolidide and 3,3-dimethyl-pent-4-enoic acid morpholide.

Examples of suitable carbon tetrahalides of the formula III are carbon tetrachloride, carbon tetrabromide and bromotrichloromethane.

The starting materials of the formulae II and III may be reacted in stoichiometric amounts. However, it is advantageous to employ the starting material of the formula III in excess, ie. in general in an amount of from 1 to 20 moles, advantageously from 3 to 10 moles, per mole of starting material of the formula II.

Suitable initiators for the reaction of the carboxylic acid amides with the carbon tetrahalides to give iminium salts are orgaic peroxides or per-esters, eg. di-tert.-butyl peroxide, dibenzoyl peroxide or tert.-butyl 2-ethyl-hexanepercarboxylate, azo-bis-isobutyronitrile or Redox systems which contain iron ions and/or copper ions, eg. $Fe^{3+}/Fe^{2+}$, $Cu^{2+}/Cu^{1+}$ or $Cu^{2+}/Fe^{2+}$; ultraviolet light may also be used to initiate the reaction. From 0.01 to 0.5 mole, preferably from 0.05 to 0.2 mole, of initiator is added per mole of carboxylic acid amide of the formula II.

Suitable organic diluents and solvents are aliphatic and aromatic hydrocarbons and chlorohydrocarbons, eg. heptane, cyclohexane, benzene, toluene and chlorobenzene. However, it is advantageous to use an excess of the carbon tetrahalide of the formula III as the solvent. The amount of solvent relative to compound of the formula II may vary within a wide range and may be from 100 to 2,000% by weight, advantageously from 500 to 1,000% by weight, based on carboxylic acid amide.

The reaction of the carboxylic acid amide of the formula II with a carbon tetrahalide of the formula III to give an iminium salt of the formula IV is carried out at from 120° to 160° C., preferably from 130° to 150° C., under atmospheric or superatmospheric pressure, batchwise or continuously. If the reaction is carried out under atmospheric pressure with reactants and/or solvents boiling below 120° C., the reaction mixture is heated from room temperature to the reaction temperature over from 1 to 20 hours, whilst simultaneously distilling off the excess reactant. If the reaction is carried out in the presence of peroxides or per-esters which decompose above 70° C., it is advisable first to heat the reaction mixture for from 1 to 15 hours at from 70° to 120° C. and then to heat it at from 120° to 160° C. If ultraviolet light is used to initiate the reaction, it suffices to keep the mixture initially at 20° C. for 10-20 hours and then to heat to 120°-160° C.

The iminium salts of the formula IV obtained by reacting a carboxylic acid amide of the formula II with a carbon tetrahalide of the formula III are novel compounds. In formula IV, X is halogen, preferably chlorine or bromine, and the halogen substituents of the vinyl group may differ from one another and from the anion. $R^1$ and $R^2$ in formula IV are each alkyl of 1 to 4 carbon atoms, especially methyl. $R^3$ and $R^4$ may be alkyl of 1 to 4 carbon atoms, especially methyl, ethyl or isopropyl, aralkyl of 7 to 9 carbon atoms, especially benzyl, or aryl of 6 to 10 carbon atoms, especially phenyl. $R^3$ and $R^4$ may also, together with the nitrogen on which they are present as substituents, form a 5-membered or 6-membered ring which may contain a further hetero-atom, especially oxygen. Examples of such rings are pyrrolidine, piperidine and morpholine.

The iminium salts of the formula IV can be converted to the compounds of the formula I by treatment with an equal to 20-fold, preferably a 3-fold - 5-fold, amount by weight of water at from 20° to 150° C., preferably from 80° to 100° C., under atmospheric or superatmospheric pressure. This hydrolysis may be carried out in the presence of the organic diluent or solvent in whose presence the iminium salt was synthesized. The resulting tetrahydrofuranones of the formula I can be isolated in a conventional manner by separating them from the aqueous phase or by extraction from the aqueous reaction mixture, and can be purified by distillation or crystallization.

The Examples which follow illustrate the process according to the invention.

EXAMPLE 1

310 g (2 moles) of 3,3-dimethyl-pent-4-enoic acid, N,N-dimethylamide and 46 g (0.2 mole) of tert.-butyl 2-ethylhexanepercarboxylate are added continuously, over 3 hours, to 3,080 g (20 moles) of carbon tetrachloride at 70°-75° C., whilst stirring. The mixture is then stirred for 2 hours at 75°-80° C., after which carbon tetrachloride is distilled off until the internal temperature reaches 140° C., the amount distilled being 2,661 g (17.26 moles). The mixture is then stirred for 4 hours at 140° C., 1,500 g of water are added and the batch is stirred for 1 hour at 90° C. When it has cooled, the lower phase of the reaction mixture is separated off and distilled. 351 g (1.68 moles) of 5-(2,2-dichlorovinyl)-4,4-dimethyltetrahydrofuran-2-one, of boiling point 101° C./0.27 mbar, are obtained, corresponding to a yield of 84% of theory.

$C_8H_{10}O_2Cl_2$ (209): calculated: C, 45.96%; H, 4.82%; Cl, 33.91%. found: C, 46.3%; H, 4.9%; Cl, 34.5%.

NMR (220 MHz): 3H 1.05 ppm (s); 3H 1.22 ppm (s); 2H 2.45 ppm (dd); 1H 4.95 ppm (d); 1H 5.98 ppm (d). $n_D^{20}$: 1.4989

EXAMPLE 2

A mixture of 40 g (0.26 mole) of 3,3-dimethylpent-4-enoic aicd N,N-dimethylamide, 231 g (1.5 moles) of carbon tetrachloride and 7 g (0.05 mole) of di-tert.-butyl peroxide is stirred for 6 hours at 140° C. in a stainless steel autoclave. 180 g (1.17 mole) of carbon tetrachloride are then distilled from the reaction mixture under reduced pressure, and the residue is stirred with 200 g of water for 1 hour at 80°-90° C. Extraction with methylene chloride, and subsequent distillation of the methylene chloride solution, gives 39 g (0.19 mole) of 5-(2,2-dichlorovinyl)-4,4-dimethyltetrahydrofuran-2-one, of boiling point 101° C./0.27 mbar.

EXAMPLE 3

A solution of 132 g (0.4 mole) of carbon tetrabromide in 250 ml of chlorobenzene is stirred at 130° C. A mixture of 31 g (0.2 mole) of 3,3-dimethyl-pent-4-enoic acid N,N-dimethylamide and 3 g (0.02 mole) of di-tert.-butyl peroxide is added dropwise over 1 hour, and the mixture is then stirred for 1 hour at 130° C. Thereafter the reaction mixture is cooled and stirred with 300 ml of water, the aqueous solution is separated off and the organic phase is distilled. 80 g (0.24 mole) of carbon tetrabromide are recovered.

The aqueous solution which has been separated off is stirred for 2 hours at 80°-90° C., allowed to cool and extracted with methylene chloride. After distilling the methylene chloride from the extract, 30 g (0.1 mole) of 5-(2,2-dibromovinyl)-4,4-dimethyl-tetrahydrofuran-2-one, of melting point 73°-74° C., are obtained.

$C_8H_{10}Br_2$ (298): calculated: C, 32.25%; H, 3.38%; Br, 53.63%. found: C, 32.8%; H, 3.4%; Br, 52.9%.

NMR (100 MHz): 3H 1.08 ppm (s); 3H 1.23 ppm (s); 2H 2.4 ppm (d); 1H 4.75 ppm (d); 1H 6.45 ppm (d).

EXAMPLE 4

124 g (0.8 mole) of 3,3-dimethyl-pent-4-enoic acid N,N-dimethylamide, 1,600 g (10.4 moles) of carbon tetrachloride and 8 g of benzoyl peroxide are stirred for 7 hours at 75°-80° C. A further 8 g of benzoyl peroxide are then added and heating at 75°-80° C. is continued for a further 7 hours. On subsequently raising the bath temperature to 150° C., 51 g of 3,3-dimethyl-pent-4-enoic acid N,N-dimethylamide are recovered in addition to the excess carbon tetrachloride. When the residue has cooled, N,N-dimethyl-[5-(2,2-dichlorovinyl)-4,4-dimethyl-tetrahydrofur-2-yl]-iminium chloride crystallizes out as a hygroscopic substance of melting point 73°-78° C.

$C_{10}H_{16}ONCl_3$ (272.5): calculated: C, 44.0%; H, 5.87%; N, 5.14%; Cl, 39.1%. found: C, 44.7%; H, 6.4%; N, 5.1%; Cl, 35.1%.

The chloride is stirred for 3 hours in 250 ml of water at 90° C. The organic phase is separated off and distilled, giving 84 g (0.4 mole) of 5-(2,2-dichlorovinyl)-4,4-dimethyl-tetrahydrofuran-2-one.

EXAMPLE 5

31 g (0.2 mole) of 3,3-dimethyl-pent-4-enoic acid, N,N-dimethylamide are added dropwise, in the course of 3 hours, to a solution of 1 g of azo-bis-isobutyronitrile in 308 g (2 moles) of carbon tetrachloride at 75°–80° C. The mixture is stirred for 1.5 hours at 75°–80° C., a further 1 g of azo-bis-isobutyronitrile is added, and the temperature is maintained for a further 2 hours. After distilling off the unconverted starting materials at a bath temperature not exceeding 150° C., a residue is left, and this is stirred with 100 ml of water at 80°–90° C. for 1 hour. 17 g (0.08 mole) of 5-(2,2-dichlorovinyl)-4,4-dimethyl-tetrahydrofuran-2-one are thereby obtained as a water-insoluble phase.

EXAMPLE 6

A solution of 31 g (0.2 mole) of 3,3-dimethylpent-4-enoic acid N,N-dimethylamide in 436 g (2.83 moles) of carbon tetrachloride is irradiated for 15 hours at 20° C. with a 300 W mercury high-pressure lamp. On distilling the reaction solution, excess carbon tetrachloride and 19 g of 3,3-dimethyl-pent-4-enoic acid N,N-dimethylamide are recovered, and at 130°–137° C./0.013 mbar 10 g of N,N-dimethyl-[5-(2,2-dichlorovinyl)-4,4-dimethyltetrahydrofur-2-yl]-iminium chloride are obtained.

To identify the salt, the perchlorate is precipitated by dissolving the chloride in water and adding perchloric acid. The perchlorate melts at 158°–160° C. and gives the following analytical data:

$C_{10}H_{16}O_5NCl_3$ (336.5): calculated: N, 4.16%; Cl, 31.65%. found: N, 3.9%; Cl, 31.1%.

NMR (270 MHz): 3H 1.22 ppm (s); 3H 1.35 ppm (s); 2H 3.3ppm (dd); 3H 3.38 ppm (s); 3H 3.42 ppm (s); 1H 5.55 ppm (d); 1H 6.15 ppm (d).

On heating 9 g of chloride in 50 ml of water for one hour at 90° C., 5 g of 5-(2,2-dichlorovinyl)-4,4-dimethyl-tetrahydrofuran-2-one are obtained as a water-insoluble phase.

We claim:

1. A process for the preparation of a 5-(2,2-dihalovinyl)-4,4-dialkyl-tetrahydrofuran-2-one of the formula I

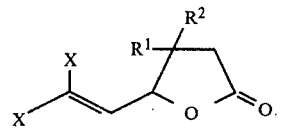

where $R^1$ and $R^2$ are each alkyl of 1 to 4 carbon atoms and X is halogen, wherein a carboxylic acid amide of the formula II

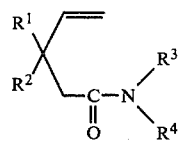

where $R^1$ and $R^2$ are each alkyl of 1 to 4 carbon atoms and $R^3$ and $R^4$ are each alkyl of 1 to 4 carbon atoms, aralkyl of 7 to 9 carbon atoms or aryl of 6 to 10 carbon atoms or together with the nitrogen on which they are present as substituents form a 5-membered or 6-membered saturated ring which may contain a further hetero-atom, is reacted with a carbon tetrahalide of the formula III $CX_4$ (III)

where X is halogen, in the presence of an initiator and of an organic diluent or solvent, at from 120° to 160° C., to give an iminium salt of the formula IV

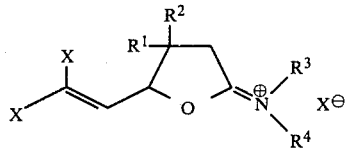

where $R^1$, $R^2$, $R^3$, $R^4$ and X have the above meanings, and this iminium salt is subsequently hydrolyzed.

2. A process as set forth in claim 1, wherein $R^3$ and $R^4$ together with the nitrogen atom on which they are present as substituents form a pyrrolidine, piperidine or morpholine ring.

3. A process as set forth in claim 1 wherein $R^3$ and $R^4$ are each alkyl of 1 to 4 carbon atoms, aralkyl of 7 to 9 carbon atoms or aryl of 6 to 10 carbon atoms.

* * * * *

UNITED STATES PATENT AND TRADEMARK OFFICE
CERTIFICATE OF CORRECTION

PATENT NO. : 4,324,725
DATED : April 13, 1982
INVENTOR(S) : Rudolf KROPP et al.

It is certified that error appears in the above-identified patent and that said Letters Patent is hereby corrected as shown below:

IN THE ABSTRACT:

Delete the first formula and substitute the following:

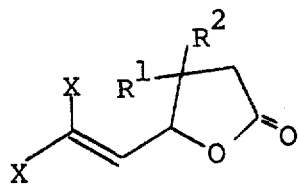

IN FOREIGN PATENT DOCUMENTS:

52-57163 should read: 7757163
52-83457 should read: 7783457
52-83459 should read: 7783459

Signed and Sealed this

Seventh Day of February 1984

[SEAL]

Attest:

GERALD J. MOSSINGHOFF

Attesting Officer          Commissioner of Patents and Trademarks